(12) United States Patent
Pou et al.

(10) Patent No.: US 6,365,100 B1
(45) Date of Patent: Apr. 2, 2002

(54) POLYMETHYLENEPOLYAMINE DIPROPIONAMIDES AS ENVIRONMENTALLY SAFE INHIBITORS OF THE CARBON CORROSION OF IRON

(75) Inventors: Tong Eak Pou, Courdimanche; Stephane Fouquay, Mont Saint Aignan, both of (FR)

(73) Assignee: CECA, S.A., Puteaux (FR)

(*) Notice: Subject to any disclaimer, the term of this patent is extended or adjusted under 35 U.S.C. 154(b) by 0 days.

(21) Appl. No.: 09/355,826

(22) PCT Filed: Jan. 9, 1998

(86) PCT No.: PCT/FR98/00036

§ 371 Date: Sep. 20, 1999

§ 102(e) Date: Sep. 20, 1999

(87) PCT Pub. No.: WO98/35072

PCT Pub. Date: Aug. 13, 1998

(30) Foreign Application Priority Data

Feb. 5, 1997 (FR) .............................. 97 01298

(51) Int. Cl.[7] .......................... C23F 11/04; C09K 3/00; C09K 15/22
(52) U.S. Cl. ........................... 422/12; 422/7; 252/390; 252/401; 510/258; 510/264; 507/241
(58) Field of Search .................. 252/390, 392, 252/394, 401, 403, 405; 422/12, 7; 510/258, 264, 401; 507/239, 241, 244

(56) References Cited

U.S. PATENT DOCUMENTS

| | | | |
|---|---|---|---|
| 2,315,871 A | | 4/1943 | Oberfell et al. |
| 3,048,620 A | | 8/1962 | Spivack |
| 3,445,441 A | * | 5/1969 | Rushton |
| 3,522,205 A | | 7/1970 | Gobran et al. |
| 3,630,659 A | | 12/1971 | Hendricks et al. |
| 4,416,729 A | * | 11/1983 | Killat et al. .............. 162/164.3 |
| 4,902,838 A | | 2/1990 | Manzer et al. |
| 4,994,575 A | * | 2/1991 | Bardasz ..................... 548/352 |
| 5,091,600 A | | 2/1992 | Moore et al. |
| 5,300,235 A | | 4/1994 | Clewlow et al. |
| 5,427,999 A | | 6/1995 | Clewlow et al. |

FOREIGN PATENT DOCUMENTS

| | | |
|---|---|---|
| EP | 365 296 A1 | 4/1990 |
| EP | 520 761 A2 | 12/1992 |
| EP | 526 251 A1 | 2/1993 |
| EP | 567 212 A1 | 10/1993 |

OTHER PUBLICATIONS

International Search Report for International Application No. PCT/FR98/00036, Form PCT/ISA/210, dated May 8, 1998. (3 pages).

* cited by examiner

*Primary Examiner*—Joseph D. Anthony
(74) *Attorney, Agent, or Firm*—Smith, Gambrell & Russell LLP

(57) ABSTRACT

Polymethylenepolyaminedipropionamides are carbonic corrosion inhibitors devoid of toxicity to the marine environment.

4 Claims, No Drawings

POLYMETHYLENEPOLYAMINE DIPROPIONAMIDES AS ENVIRONMENTALLY SAFE INHIBITORS OF THE CARBON CORROSION OF IRON

TECHNICAL FIELD

In the production of petroleum and gas, corrosion caused by carbon dioxide, which is known as carbonic corrosion, takes place at the bottom of wells, where the temperature is generally about 60° C. or more, in the surface pipelines and in refining of the crude oil. The approach usually adopted to overcome this is to use corrosion inhibitors based on amine salts, quaternary ammonium salts, imidazolines or phosphoric esters, but these compounds are not entirely satisfactory since they are ecotoxic in marine environments (acute toxicity to Skeletonema costatum at less than 1 ppm).

BACKGROUND ART

In European patent applications EP-A-520,761 and EP-A-526,251, it is mentioned that it is possible to reduce the toxicity of a diamine or of an imidazoline by reacting these molecules with acrylic acids; the larger the number of acrylic acid molecules, the more the toxicity reduces.

European patent EP-A-567,212 is based on the low toxicity of morpholine salts and phosphoric esters.

DISCLOSURE OF INVENTION

It has now been found that good inhibition of the carbonic corrosion of iron may be obtained with non-ecotoxic compounds of water-soluble polymethylenepolyaminodipropionamide type having a very low marine ecotoxicity (50 to 100 ppm on Skeletonema costatum), the general formula of which compounds is:

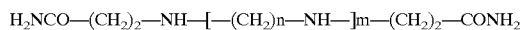

$H_2NCO-(CH_2)_2-NH-[-(CH_2)n-NH-]m-(CH_2)_2-CONH_2$ in which m is an integer which may take any value from 1 to 4, which represents the number of polymethyleneamino $-(CH_2)_n-NH-$ chain units, it being possible for n to have, in each polymethyleneamino chain unit, an integer value from 2 to 6. This process for limiting the carbonic corrosion of steel in aqueous media forms the basis of the present invention, this process consisting in using, as non-ecotoxic corrosion inhibitor, an aqueous composition containing as active material at least one of the said polymethylenepolyaminodipropionamides, with the exception of tripropylenetetraaminedipropionamide. These compounds may be taken individually or as a mixture, and moreover the corresponding technical products are themselves mixtures of such individual compounds.

These polymethylenepolyaminodipropionamides are readily obtained by condensation of acrylamide with polymethylene-polyamine bases, for example the EDA, DETA, TETA, TEPA and HEPA bases in the ethyleneimine series, the PDA and DPTA (norspermidine) bases in the propyleneimine series, or hybrid compounds, for example of the spermine $H_2N-(CH_2)_3-NH-(CH_2)_4-NH-(CH_2)_3-NH_2$, or spermidine $H_2N-(CH_2)_4-NH-(CH_2)_3-NH_2$ type.

They are fully characterized by NMR spectrography (see Table I later).

These compounds may be used both in continuous injection and in a batchwise treatment. The useful doses are between 5 ppm and 20 ppm. They may be used directly or in the form of an aqueous or aqueous-alcoholic solution, preferably an aqueous-glycolic solution for flash-point reasons, containing from 20% to 65% by weight.

EXAMPLES

The examples which follow are intended to give a better understanding of the invention and its advantages.

Example 1

Preparation of Polymethylenepolyaminedipropionamides

The preparation of three molecules tested in Examples 2 and 3 below is described here.

Molecule A is the diamide $H_2NCO-(CH_2)_2-NH-[-(CH_2)_2-NH-]_2-(CH_2)_2-CONH_2$ (RN 92009-86-4), Molecule B is the diamide $H_2NCO-(CH_2)_2-NH-[-(CH_2)_2-NH-]_3-(CH_2)_2-CONH_2$, Molecule C is the diamide $H_2NCO-(CH_2)_2-NH-(CH_2)_3-NH-(CH_2)_2-NH-(CH_2)_3-NH-(CH_2)_2-CONH_2$, A, B and C are obtained by condensation of acrylamide with a polyamine, diethylenetriamine, triethylenetetraamine and bis(propylamino)ethylenediamine respectively, according to the following procedure.

Compounds Charged:
Acrylamide 2 mol
Polyamine 1 mol
Water 7% by weight of the total charge
Ethylene glycol 28% by weight of the total charge Procedure:
Charge the amine, the water and the ethylene glycol into the reactor and heat to 60° C. under a stream of nitrogen.
At this temperature, introduce the acrylamide over about 2 hours.
Keep the mixture steady at 60° C. for 5 hours.
Monitor the reaction progress by $^1H/^{13}C$ NMR.
Recover the polymethylenepolyaminedipropionamides directly in the form of solution.

The $^1H/^{13}C$ NMR characteristics of products A, B and C will be found in Table I, in which (s) means singlet, (t) means triplet and (m) means multiplet.

TABLE I

NMR spectral characteristics of compounds A, B and C (200 MHz $^1H$ spectrometer)

Compound A

| 1 | 2 | 3 | | 4 | 5 | | 5 | 4 | | 3 | 2 | 1 | |
|---|---|---|---|---|---|---|---|---|---|---|---|---|---|
| H2N | CO | CH2 | CH2 | NH | CH2 | CH2 | NH | CH2 | CH2 | NH | CH2 | CH2 | CO | NH2 |

M: 245.32 g.mol$^{-1}$; $C_{10}H_{23}N_5O_2$
Yield (%) = 97
$^1H$ NMR (D$_2$O): 2.34 (t, 4H, H$_2$); 2.58 (s, 8H, H$_4$ and H$_5$); 2.73 (t, 4H, H$_3$)
$^{13}C$ NMR (D$_2$O): 36.7 (C$_2$); 46.7 (C$_3$); 49.6 m, C$_4$ and C$_5$); 179.6 (C$_1$)

TABLE I-continued

NMR spectral characteristics of compounds A, B and C (200 MHz $^1$H spectrometer)

Compound B

```
     1    2    3         4    5         6    6         5    4         3    2    1
H2N  CO   CH2  CH2  NH   CH2  CH2  NH   CH2  CH2  NH   CH2  CH2  NH   CH2  CH2  CO   NH2
```
M: 288.39 g.mol$^{-1}$; $C_{12}H_{28}N_6O_2$
Yield (%) = 94
$^1$H NMR (D$_2$O): 2.34 (t, 4H, H$_2$); 2.58 (s, 12H, H$_4$ to H$_6$); 2.73 (t, 4H, H$_3$)
$^{13}$C NMR (D$_2$O): 36.7 (C$_2$); 46.7 (C$_3$); 49.6 (m, C$_4$ to C$_6$); 179.6 (C$_1$)

Compound C

```
     1    2    3         4    5    6         7    7         6    5    4         3    2    1
H2N  CO   CH2  CH2  NH   CH2  CH2  CH2  NH   CH2  CH2  NH   CH2  CH2  CH2  NH   CH2  CH2  CO   NH2
```
M: 316.45 g.mol$^{-1}$; $C_{14}H_{32}N_6O_2$
Yield (%) = 90
$^1$H NMR (D$_2$O): 2.34 (t, 4H, H$_2$); 2.58 (s, 12H, H$_4$ to H$_6$); 2.73 (t, 4H, H$_3$)
$^{13}$C NMR (D$_2$O): 30.5 (C$_5$); 36.9 (C$_2$); 46.7 (C$_3$) 48.7 (m, C$_4$ and C$_6$); 49.6 (C$_7$); 179.5 (C$_1$)

Comments: In all cases, the coupling constant JH$_2$H$_3$ is 7 Hz

It is noted in passing that compound B H$_2$NCO—(CH$_2$)$_2$—NH—[—(CH$_2$)$_2$—NH—]$_3$(CH$_2$)$_2$—CONH$_2$ is a new product. It is also a subject of the present invention.

Example 2

The experimental procedures intended to evaluate the corrosion-inhibitory efficiencies in carbon dioxide-saturated medium of the products used (A, B and C of Example 1) are described in this example. In order to simulate the corrosive medium, a solution of NACE type containing 50 g/l of NaCl and 0.25 mg/l of acetic acid, saturated by continuously bubbling CO$_2$ through, depending on the case, and with inhibitor added or not added, is used.

Experimental Procedures

The process is performed in a thermostatically regulated 600 ml Pyrex cell including, besides a gas inlet and outlet, three electrodes coupled to the cell by ground joints, namely a carbon-steel working electrode whose surface of contact with the corrosive solution is 1 cm$^2$, a saturated calomel reference electrode and a platinum counterelectrode having a very large surface of contact with the corrosive solution. 500 ml of the corrosive solution is placed in the cell, as control or with inhibitor added, after which the counterelectrode and the reference electrode are put in place. The solution is de-aerated by bubbling nitrogen through for one hour and is then saturated with CO$_2$ by bubbling for at least one hour. In order to ensure good saturation with CO$_2$, this gas is left to bubble through throughout the experiment.

The rate of corrosion V$_{corr}$ is measured by a method of measuring polarization resistance, which is known in the art. The corrosion rate reading is taken after stabilization for 6 hours.

The percentage of protection (%P) which allows the corrosion-inhibitory efficiency of the test product to be expressed is given by the relationship:

$$\%P=\{(V^0{}_{corr}-V^i{}_{corr})/V^0{}_{corr}\}\times 100$$

where $V^0{}_{corr}$=rate of corrosion without inhibitor $V^i{}_{corr}$=rate of corrosion in the presence of a dose of inhibitor.

Table II collates the percentages of protection at room temperature (25° C.) as a function of the nature of the polymethylenepolyaminodipropionamides used and their dose.

TABLE II

Carbonic corrosion-inhibitory efficiencies

| | PERCENTAGE OF PROTECTION (%) | | | |
|---|---|---|---|---|
| Molecules/dose (ppm) | 10 | 20 | 50 | 100 |
| A | 24 | 44 | 48 | 53 |
| B | 34 | 43 | 48 | 56 |
| C | 63 | 70 | 73 | 82 |

Example 3

The ecotoxicity measurements for various polymethylenepolyaminedipropionamides were carried out on a bacterium (Photobacterium phosphoreum) and on an alga (Skeletonema costatum). The bacterial test is the Microtox test carried out according to AFNOR standard NF T90-320. The toxicities on Skeletonema costatum are determined according to the method ISO/DIS 10253. The Microtox toxicity is expressed as LC$_{50}$ (lethal concentration in mg/l to destroy 50% of the population in 15 minutes). On Skeletonema costatum, the toxicity is expressed as EC$_{50}$ (effective concentration in mg/l to inhibit the growth of 50% of the population in 72 hours).

Table III gives the toxicities obtained for compounds A, B and C.

TABLE III

| Toxicity | Microtox (LC$_{50}$) in mg/l | Skeletonema costatum (EC$_{50}$) in mg/l |
|---|---|---|
| A | 128 | 50 to 100 |
| B | 104 | 50 to 100 |
| C | 127 | 5–10 |

What is claimed is:

1. Process for limiting the carbonic corrosion of steel in aqueous media, wherein said process comprises adding to a steel containing aqueous media an aqueous composition comprising a non-ecotoxic corrosion inhibitor which is at least one of the polymethylenepolyaminedipropionamides compounds corresponding to the formula:

H$_2$NCO—(CH$_2$)$_2$—NH—(—(CH$_2$)n—NH—)m—(CH$_2$)$_2$—CONH$_2$ in which m is an integer from 1 to 4, which represents the number of polymethyleneamino —(CH$_2$)n—NH— chain units, n having, in each polymethyleneamino chain unit, an integer value from 2 to 6, with the proviso that the polymethylenepolyaminedipropionamide compound is not tripropylenetetraamine dipropionamide.

2. Process according to claim 1, wherein the molecule used is diethylenetriaminedipropionamide of formula:

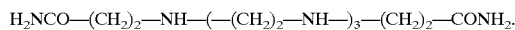

3. Process according to claim 1, wherein the molecule used is triethylenetetraaminedipropionamide of formula:

4. Non-ecotoxic inhibitor of the carbonic corrosion of steel in aqueous media, consisting of an aqueous or aqueous-alcoholic solution containing 20–65% by weight of at least one compound corresponding to the formula:

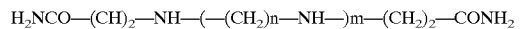

in which m is an integer from 1 to 4, n having, in each polymethyleneamino chain unit, an integer value from 2 to 6, with the proviso that the polymethylenepolyaminedipropionamide compound is not tripropylenetetraamine dipropionamide.

* * * * *